United States Patent
Andersson et al.

(10) Patent No.: US 6,783,570 B1
(45) Date of Patent: Aug. 31, 2004

(54) METHOD FOR DETERMINING THE NEEDED AMOUNT OF STRUCTURE MODIFYING AGENT TO BE ADDED TO CAST IRON

(75) Inventors: Conny Andersson, Eskilstuna (SE);
Patrik Popelar, Katrineholm (SE);
Tom Schroeder, Auburn Hills, MI (US)

(73) Assignee: SinterCast AB, Stockholm (SE)

(*) Notice: Subject to any disclaimer, the term of this patent is extended or adjusted under 35 U.S.C. 154(b) by 0 days.

(21) Appl. No.: 09/868,062
(22) PCT Filed: Dec. 16, 1999
(86) PCT No.: PCT/SE99/02392
§ 371 (c)(1),
(2), (4) Date: Sep. 14, 2001
(87) PCT Pub. No.: WO00/37698
PCT Pub. Date: Jun. 29, 2000

(30) Foreign Application Priority Data

Dec. 18, 1998 (SE) .............................. 98044191

(51) Int. Cl.⁷ .................................. C21C 1/10
(52) U.S. Cl. .................. 75/377; 73/864.1; 164/4.1; 266/79; 266/80; 374/139; 700/204

(58) Field of Search .............................. 75/377; 266/79, 266/80; 73/864.91; 164/4.1; 374/139; 700/204

(56) References Cited

U.S. PATENT DOCUMENTS 6,571,856 B1 * 6/2003 Popelar et al. ............... 164/4.1
6,604,016 B1 * 8/2003 Andersson ................... 700/204

FOREIGN PATENT DOCUMENTS

| WO | WO 96/01755 | 3/1986 |
| WO | WO 91/13176 | 9/1991 |
| WO | WO 92/06809 | 4/1992 |

* cited by examiner

Primary Examiner—Melvyn Andrews
(74) Attorney, Agent, or Firm—Nixon & Vanderhye P.C.

(57) ABSTRACT

The present invention provides a possibility to evaluate cooling curves recorded in near-eutectic cast iron melts. The curves are evaluated by generated in the melt in the center of the sample to the melt as a function of time. This information is then used to identify the part of the centrally recorded cooling curve that can be used as a basis for determining the amount of structure-modifying agent that must be added to produce compacted graphite cast iron, and/or spheroidal graphite cast iron, and to identify the part of said curve that is associated with formation of primary austenite.

6 Claims, 6 Drawing Sheets

FIG.6 ed in WO86/01755, WO92/06809, WO91/
METHOD FOR DETERMINING THE NEEDED AMOUNT OF STRUCTURE MODIFYING AGENT TO BE ADDED TO CAST IRON

This application is the National Phase of International Application PCT/SE99/02392 filed Dec. 16, 1999 which designated the U.S. and that International Application was published under PCT Article 21(2) in English.

The present invention relates to an improved method for predicting the microstructure in which a cast iron melt, having a composition with a carbon equivalent near the eutectic point of the iron-carbon phase diagram, will solidify. The invention also relates to an apparatus for carrying out the method.

BACKGROUND OF THE INVENTION

WO86/01755 (incorporated by reference) discloses a method for producing compacted graphite cast iron by using thermal analysis. A sample is taken from bath of molten cast iron and this sample is permitted to solidify during 0.5 to 10 minutes. The temperature is recorded simultaneously by two temperature-responsive means, one of which is arranged in the centre of the sample and the other in the immediate vicinity of the vessel wall. So-called cooling curves representing temperature of the iron sample as a function of time are recorded for each of the two temperature-responsive means. According to this document, it is then possible to determine the necessary amount of structure-modifying agents that must be added to the melt in order to obtain the desired microstructure. However, the cooling curves disclosed in this document are rather uniform and no variations are disclosed.

In order to accurately determine the graphite microstructure in cast iron specimens, conventional thermal analysis techniques, such as the one disclosed in WO 86/01755, require cooling curves where the first thermal arrest caused by austenite formation is distinctly separated from heat release caused by the onset of eutectic solidification. However, sometimes cooling curves are obtained without such a distinctly separated thermal arrest. This is the case when the molten cast iron solidifies as eutectic or hyper-eutectic iron. Until now, it has not been possible to use cooling curves corresponding to near eutectic cast iron for monitoring graphite growth.

WO93/20965 teaches that hyper-eutectic melts, where graphite nucleates before iron, do not provide a distinct plateau as the temperature crosses the liquidus line. This is correctly attributed to the fact that graphite crystallisation has a lower latent heat release than iron.

By placing a small amount of low-carbon iron in the melt, the low-carbon iron partially dissolves locally while the sample is still molten. As the sample cools, the relatively pure iron surrounding the remaining solid portion of the nail begins to solidify because of its lower carbon equivalent (CE). Ultimately, as the sample volume cools below the liquidus line, the remaining solid volume of nail, the surrounding low CE and the melted portion of the nail begin to solidify and "trigger" the solidification in an otherwise hyper-eutectic melt. The net result is that an austenite arrest plateau appears on the cooling curve.

WO93/20965 also states that the temperature difference ($\Delta T$) between $T_{67}$ and $T_{c\ max}$ can be used to establish a correlation with the carbon equivalent. However, WO93/20965 refers to hyper-eutectic melts, i.e. melts where the carbon equivalent is so high that the release of heat from the primary solidification does not coincide with the minima of the cooling curve (in the hatched region of FIG. 2(a) of WO93/20965). Accordingly, the primary solidification and the eutectic solidification are separate.

None of the above cited references discuss anything about carrying out thermal analysis on cast iron melts in order to determine the carbon equivalent of melts which are near-eutectic. Moreover, WO93/20965 suggests measurements on melts having a carbon equivalent of up to 4.7%. It is disadvantageous to reach such high values because of graphite flotation and the degeneration of graphite shape. Likewise, the method of WO93/20965 is disadvantageous in that it requires an extra addition of low-carbon steel or iron to the sampling vessel, and accordingly lead to higher costs and a more laborious method.

SUMMARY OF THE INVENTION

The present invention provides a possibility to evaluate cooling curves recorded in near-eutectic cast iron melts. The curves are evaluated by determining the net amount of heat generated in the centre of the melt sample as a function of time. This information is then used to identify the part of the centrally recorded cooling curve that can be used as a basis for determining the amount of structure-modifying agent that must be added to produce compacted graphite cast iron, and/or spheroidal graphite cast iron, and to identify the part of said curve that is associated with formation of primary austenite.

DEFECTIONS

The term "cooling curve" as utilised herein refers to graphs representing temperature as a function of time, which graphs have been recorded in the manner disclosed in WO86/01755, WO92/06809.

The term "heat generation curve" as utilised herein relates to a graph showing the heat that is generated in a certain zone of a molten cast iron. For the purposes of the present invention, all heat generation curves herein are determined for a zone located in the centre of a sample of molten cast iron. This zone is generally referred to as the "A zone".

The term "sample vessel" as disclosed herein, refers to a small sample container which, when used for thermal analysis, is filled with a sample of molten metal. The temperature is then recorded during solidification in a suitable way preferably the sample vessel is designed in the manner disclosed in WO86/01755, WO92/06809, WO91/13176 (incorporated by reference) and WO96/23206 (incorporated by reference).

The term "sampling device" as disclosed herein, refers to a device comprising a sample vessel equipped with at least two temperature responsive means for thermal analysis, said means being intended to be immersed in the solidifying metal sample during analysis, and a means for filling the sample with molten metal. The sample vessel is preferably equipped with said sensors in the manner disclosed in WO96/23206.

The term "structure-modifying agent" as disclosed herein, relates to compounds affecting the morphology of graphite present in the molten cast iron. Suitable compounds can be chosen from the group of magnesium and rare earth metals such as cerium, or mixtures of these compounds. The relationship between the concentration of structure-modifying agents in molten cast irons and the graphite morphology of solidified cast irons have already been discussed in the above cited documents WO92/06809 and WO86/01755.

The term "CGI" as utilised herein refers to compacted graphite cast iron.

The term "SGI" as utilised herein refers to spheroidal graphite cast iron.

FIGURES

The invention is described with reference to the accompanying figures, in which:

FIGS. 1A–4A disclose cooling curves. A continuos line relates to the temperature in the centre of the melt and a dashed line relates to the temperature close to the wall of the sample vessel.

FIGS. 1B–4B show A zone heat generation curves corresponding to the cooling curves in FIGS. 1A–4A. FIG. 1 relates to normal hypo-eutectic cast iron and FIGS. 2–3 show curves for near-eutectic cast irons comprising increased values of the carbon equivalent. FIG. 4 discloses curves relating to hypo-eutectic cast iron.

DETAILED DESCRIPTION OF THE INVENTION

Figure 1A:
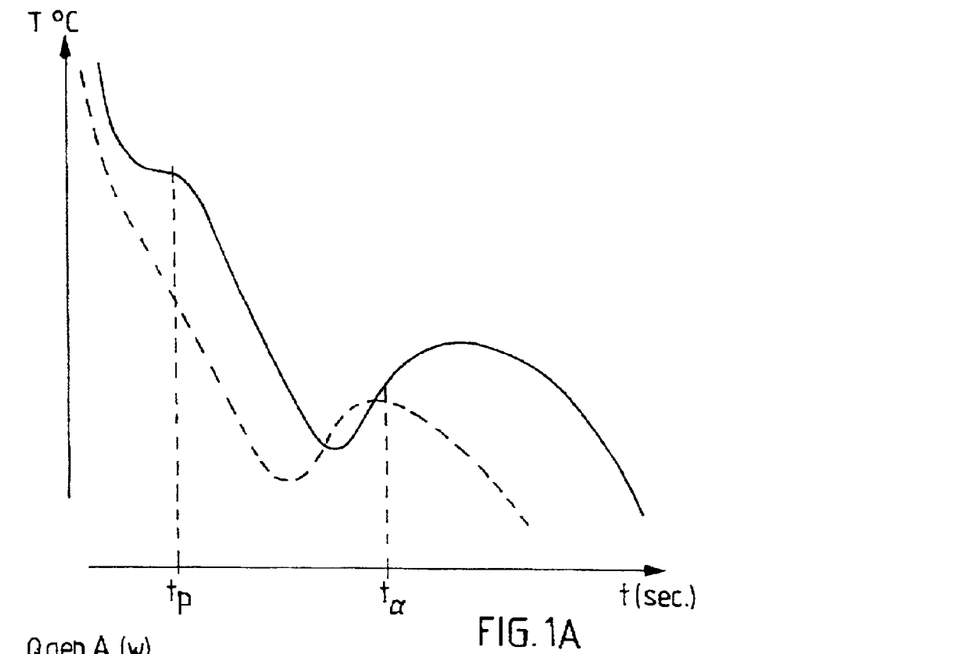
Figure 2A:
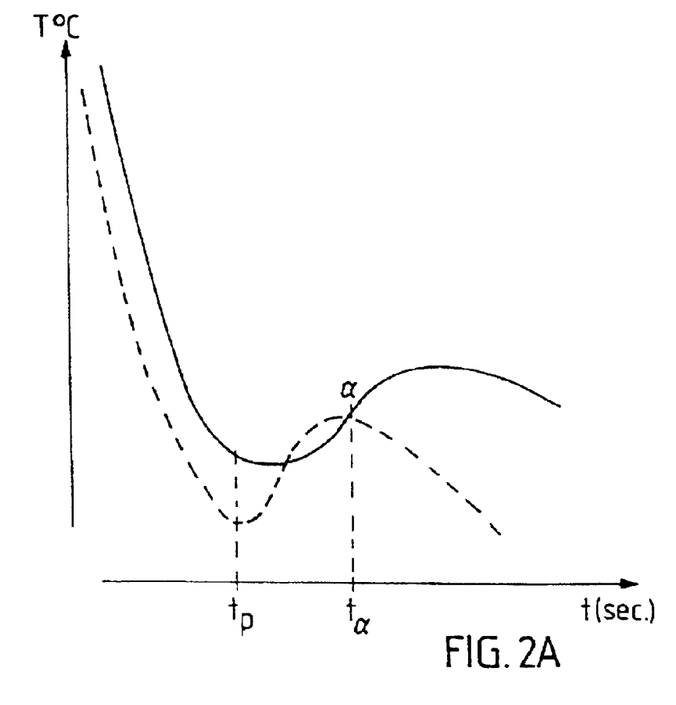
Figure 3A:
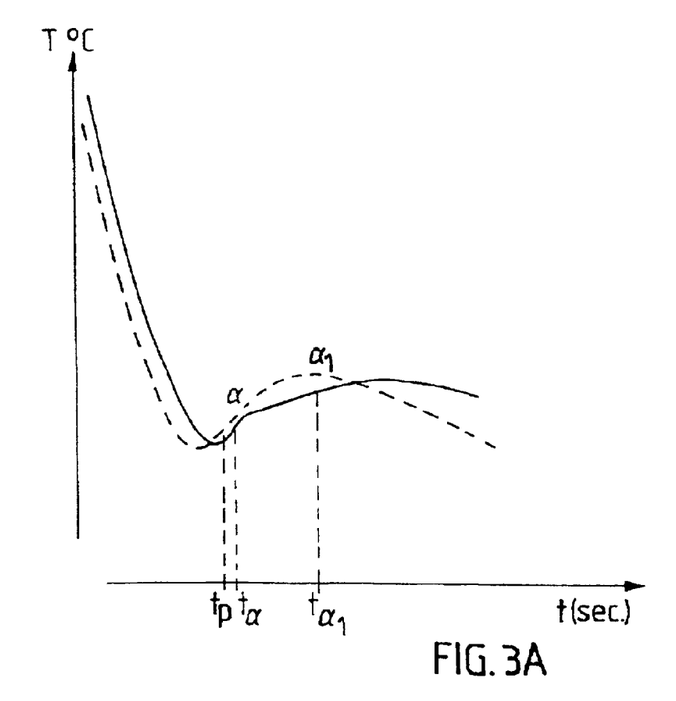

As already mentioned above, the present invention relates to an improved method for interpreting cooling curves in neareutectic cast iron melts. One of the important aspects of a cooling curve is the maximum slope of the recalescence peak of the centrally recorded cooling curve. This point is referred to as a in FIGS. 1A, 2A and 3A. In cooling curves corresponding to near-eutectic cast iron melts, the inflexion point (referred to in the figures as "$t_p$") is located much closer to α and it can be very difficult to determine the slope correctly. Examples of such curves can be found in FIGS. 2A and 3A. However, it has now turned out that the determination of the maximum slope at a can be considerably simplified if a heat generation curve corresponding to the central zone (the A zone) of the molten cast iron is calculated. Such a heat generation curve renders it possible to determine the location of $t_p$ in the centrally recorded cooling curve and to check whether it affects the slope of the recalescence peak or not.

The thermal balance of any uniform element can be described by the relation:

$$Q_{stored}=Q_{generated}+Q_{in}-Q_{out} \quad (1).$$

where $Q_{stored}$ is the amount of heat stored by the heat capacity of the material, $Q_{generated}$ is the amount of heat generated by the volume of material, $Q_{in}$ is the heat transferred into the material from its surroundings and $Q_{out}$ is the heat transferred out of the material to its surroundings.

Figure 6:
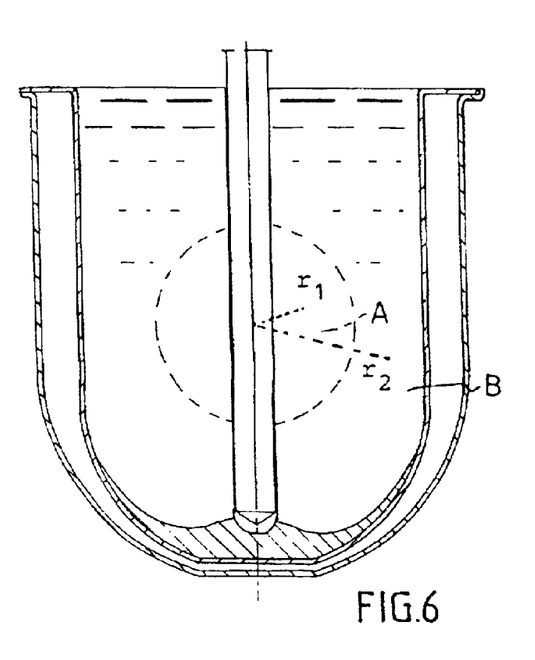
FIG. 6 is a schematic representation of a sample vessel in which the heat is approximately uniformly transported in all directions. During measurements the vessel is filled with molten cast iron. This molten cast iron can be considered as a freezing sphere. The A zone relates to a sphere in the centre of the molten sample and the B zone relates to the molten iron surrounding the A zone. The radii $r_1$ and $r_2$ relate to the mean radii of the A zone and the B zone, respectively.

When carrying out the present invention, it is advantageous to use a sample vessel as disclosed in SE 9704411-9. In such a sample vessel, the heat transport in a sample contained in the vessel is approximately the same in all directions. From now on the heat transport between the centre (FIG. 6, zone A) and the more peripheral (FIG. 6, zone B) part of a molten cast iron contained in a sample vessel is described. As the A zone is situated in the centre of the molten cast iron sample, and as that zone can be considered to be a freezing sphere, no heat is transported into the zone and $Q_{in}$ is therefore equal to zero. Appropriate substitutions in relation (1) above give the following equation:

$$C_p m_A dT_A/dt=Q_{genA}+0-4\pi ke[(T_A-T_B)/(1/r_1-1/r_2)] \quad (2)$$

where $C_p$ is the heat capacity per unit mass, $m_A$ is the mass of the A zone, $dT_A/dt$ is the temperature change of the A zone per unit time, $Q_{genA}$ is the heat generated in zone A, ke is the effective heat transfer coefficient of the material, and $(1/r_1-1/r_2)^{-1}$ is the mean distance for heat transport. The radii $r_1$ and $r_2$ are both defined in FIG. 6. $T_A$ and $T_B$ are the temperatures in the A zone and B zone respectively.

From equation (2) we can isolate the heat generation term and calculate the average bulk heat generation in the A zone:

$$Q_{genA}=C_p m_A dTA/dt+4\pi ke[(T_A-T_B)/(1/r_1-1/r_2)] \quad (3)$$

In equation (3) all variables are constants except $dT_A/dt$ and $(T_A-T_B)$. Accordingly, equation (3) can be simplified to:

$$Q_{genA}=k_1 dT_A/dt+k_2(T_A-T_B) \quad (4)$$

where $k_1$ and $k_2$ are constants. Hence, a heat release curve can be calculated from a set of cooling curves recorded in the centre and the periphery of a sample of molten cast iron.

As already mentioned, these calculations are based on a situation where heat is uniformly transported in all directions. The skilled person can of course also calculate other equations corresponding to other heat transport conditions.

Figure 1B:
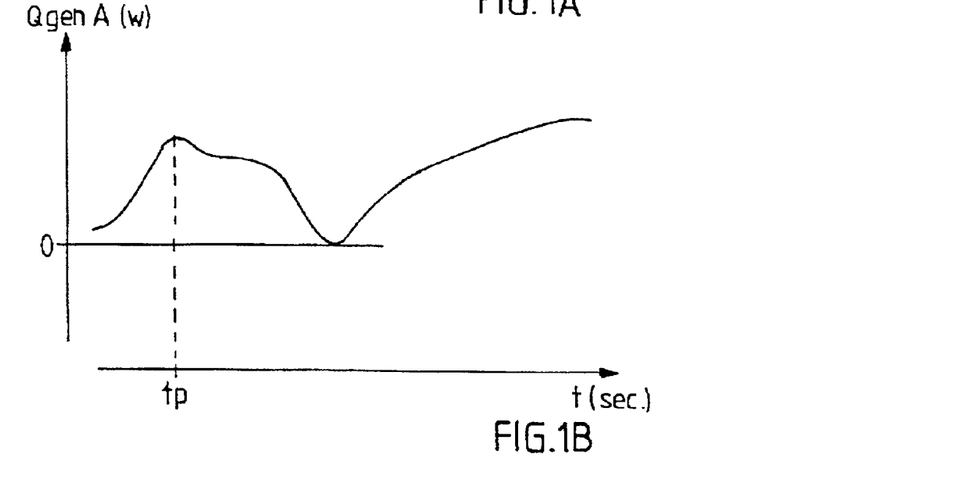

As mentioned earlier, the carbon equivalent of a certain cast iron melt affects the appearance of its corresponding cooling curves and heat release curves. Such cooling curves and heat generation curves can, depending on the carbon equivalent, be classified into one of four model types:

Type 1, which is disclosed in FIG. 1, relates to hypo-eutectic cast iron. The cooling curve recorded in the centre of the sample is characterised by a first inflexion point associated with formation of austenite, followed by a local minimum. Interpretation of such curves does not present any particular difficulties and can be carried out in accordance with the principles outlined in WO86/01755 and WO92/06809. It should be noted that there is a peak ($t_p$) on the zone A heat generation curve that corresponds to the inflexion point (and accordingly with the onset of austenite formation) on the centrally recorded cooling curve.

Figure 2B:
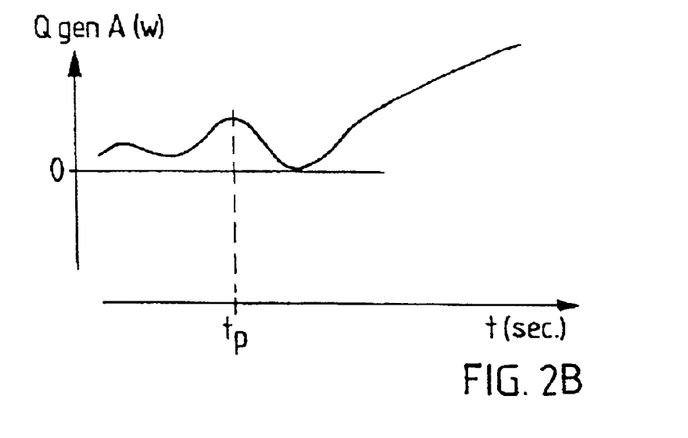

Type 2, which is disclosed in FIG. 2, relates to near-eutectic cast iron and is characterised by a very flat local minimum on the cooling curve recorded in the centre of the sample. An inflexion point cannot be seen. However, it is much easier to find a peak corresponding to the austenite formation point $t_p$ on the heat generation curve.

In this case, it turns out that the austenite formation point $t_p$ is located in connection to the local minimum resulting in a very flat minimum. From FIGS. 2A and 2B it can be seen that $t_p$ does not affect the slope at α.

Figure 3B:
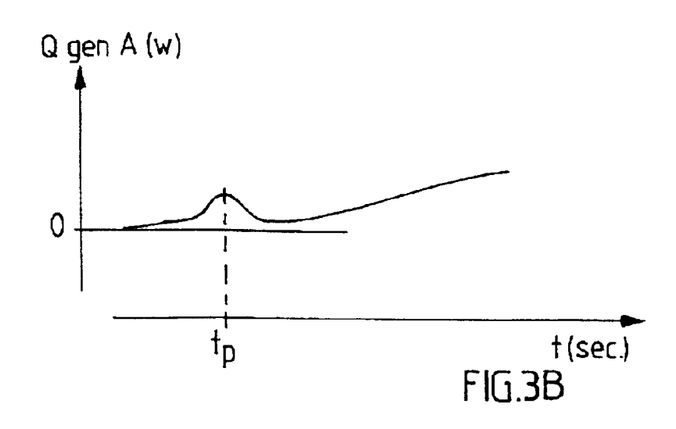

Type 3, which is disclosed in FIG. 3, also relates to near-eutectic cast iron, and is characterised by a detectable inflexion point after the local minimum in the cooling curve recorded in the centre of the sample. After determining the heat generation curve it is easy to establish the position of the austenite formation point $t_p$ to a location immediately after the local minimum. However, in this situation the recalescence, and accordingly α is affected by the austenite formation. In order to be able to disregard the effects of the "moved austenite formation point" and to find a correct α located at $t_\alpha$ (where $t_\alpha<t_p$), the part of the centrally recorded cooling curve immediately adjacent to $t_p$, and having time values t such that $t-t_p$ are larger than a predetermined threshold value tv, are searched for a maximum value $\alpha_1$ of the first time derivative. This value $\alpha_1$ is then used as a correct α in the method. A suitable threshold value tv can easily be determined by the skilled person, but typical examples of such values are 1–5 seconds.

Figure 4A:
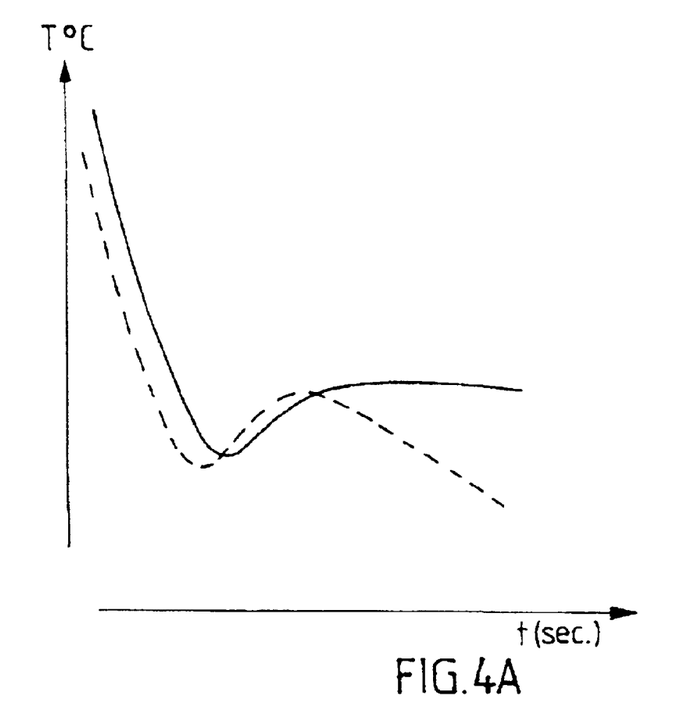
Figure 4B:
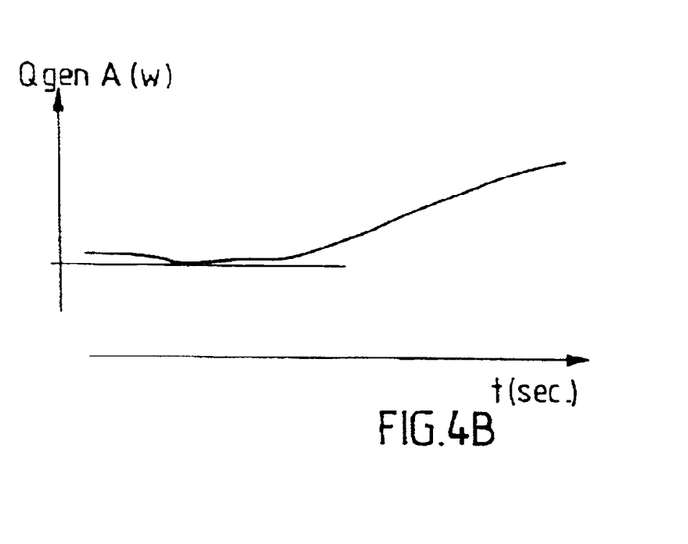
Figure 5:
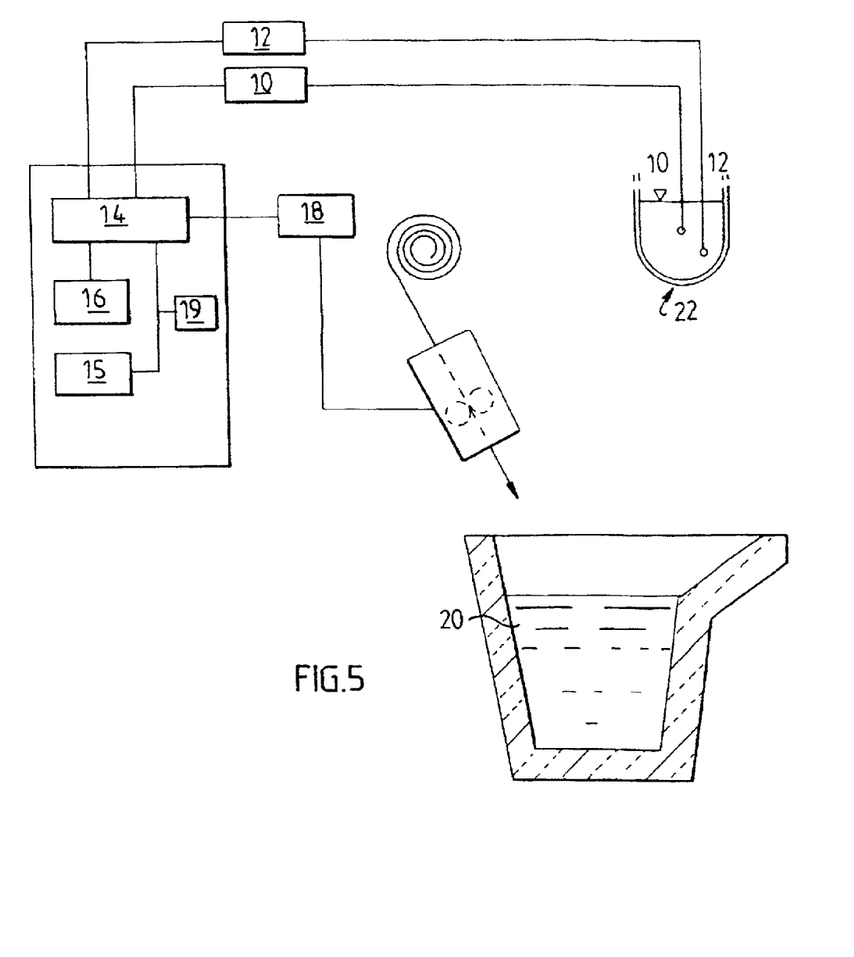
FIG. 5 is a schematic presentation of an apparatus for controlling production of compacted graphite or spheroidal graphite cast iron according to the present invention.

Type 4, which is disclosed in FIG. 4A, relates to hyper-eutectic cast iron. This type is characterised in that no evident inflexion points or wide minima can be seen. The heat generation curve of the A zone does not comprise any detectable peaks. The present invention is not applicable in this situation.

It is preferred to carry out the prediction method by using a computer-controlled system, especially when a large number of measurements must be carried out. In this case, the same kind of sampling device 22 that has been described above is used. Such a computer-controlled system is outlined in FIG. 6. During the measurement of a particular sample the two temperature-responsive means 10, 12 send signals to a computer 14 comprising a ROM unit 16 and a RAM unit 15 in order to generate the cooling curves. The computer device 14 is coupled to a memory means 19 in which a program routine is stored. When, in the following, it is described that the computer operates, it is to be understood that the computer is directed by the program in memory 19. The memory 19 may be a ROM circuit or a hard disc. The program may be supplied to the memory 19 from a non-volatile memory such as a CD-ROM or a diskette, e.g. via a databus (not shown). The computer has access to calibration data in a ROM unit 16 and calculates the amount of structure-modifing agents that must be added to the melt. This amount is signalled to a means 18 for administrating structure-modifying agent to the melt 20 to be corrected, whereby the melt is supplied with an appropriate amount of such agents.

What is claimed is:

1. A process for determining the amount of structure-modifying agent that has to be added to a certain cast iron melt in order to obtain compacted graphite cast iron or spheroidal graphite cast iron from a molten cast iron having an hypo-eutectic or close to eutectic composition, which method requires a sampling device comprising a sample vessel, means for monitoring temperature as a function of time both in the centre and close to the wall of said sample vessel, and a means for administrating structure-modifying agents to the molten cast iron, the method comprising the steps of:

a) for the chosen casting method calibrating the amount of structure-modifying agent that has to be added to a hypo-eutectic melt in order to obtain compacted graphite cast iron or spheroidal graphite cast iron as a function of the maximum value a of the first time derivative of a cooling curve recorded in the centre of a sample vessel;

b) taking a sample of the molten cast iron by using a sampling device;

c) allowing said sample to solidify in a sample vessel, aid during the solidification recording cooling curves in the centre of the sample vessel and at the sample vessel wall, respectively;

d) determining a heat generation curve disclosing the heat generated in the centre of the sample as a function of time by applying i) the thermal balance formula:

$$Q_{stored}=Q_{generated}+Q_{in}-Q_{out}$$

where $Q_{stored}$ is the amount of heat stored by the heat capacity of the material, $Q_{generate}$ is the amount of heat generated by the volume of material, $Q_{in}$ is the heat transferred into the material from its surroundings and $Q_{out}$ is the heat transferred to the surroundings; and ii) the cooling curves recorded in step c);

e) identifying the location of a possible local maximum $t_p$ on the heat generation curve obtained in step d), which maximum corresponds to an austenite formation point on the centrally recorded cooling curve obtained in step c), and controlling whether there is a risk that this austenite formation point affects the value of the maximum slope of the centrally recorded cooling curve; and f) if a $t_p$ has been located, and if there is no risk that the maximum first time derivative value α is affected by austenite formation, calculating the amount of structure-modifying agent (Va) that has to be added to the melt by using the value α and the calibration data obtained in step a); or g) if a $t_p$ has been located, and if $t_p-t_\alpha$ is less than a threshold value $t_{rv}$, identifying a time, $t_{\alpha 1}$, ($t_{\alpha 1}>t_\alpha$) for which the second time derivative of the centrally recorded cooling curve is approximately 0, determining the first time derivative value $\alpha_1$, and calculating the amount of structure-modifying agent (Va) that has to be added to the melt by using the value $\alpha_1$ and the calibration data obtained in step a).

2. A process according to claim 1, characterised in that the amount of structure-modifying agent that has to be added to a certain cast iron melt in order to obtain compacted graphite cast iron is determined.

3. A process according to claim 1 or claim 2, characterised in that the heat transport in a sample vessel containing molten cast iron is approximately the same in all directions.

4. A process for producing compacted graphite cast iron castings or spheroidal graphite cast iron castings from a molten cast iron having an eutectic or close to eutectic composition, comprising the steps of:

a) providing molten cast iron having an eutectic or close to eutectic composition;

b) determining the amount of structure-modifying agent that has to be added to a certain cast iron melt in order to obtain compacted graphite cast iron or spheroidal graphite cast iron according to the method of either claim 1 or claim 3;

c) adding the amount of structure-modifying agent determined in step b) to the molten cast iron; and d) carrying out the casting operation in a per se known manner.

5. An apparatus for establishing, in real time, an amount of a structure-modifying agents be added to a hypo-eutectic or near-eutectic cast iron melt during the process of producing a compacted graphite iron casting; the apparatus comprising:

a first temperature sensor (10) for recording a cooling curve in the centre of a sample vessel;

a second temperature sensor (12) for recording a cooling curve in the vicinity of the sample vessel wall;

a computer device (14) for determining an amount value (Va) of a structure modifying agent to be added to the melt;

a memory means (16) which is provided with pre-recorded calibration data; the computer being set up to determine the heat generated in the centre of the sample as a function of time (a heat generation curve) by applying i) the thermal balance formula:

$$Q_{stored} = Q_{generated} + Q_{in} - Q_{out}$$

where $Q_{stored}$ is the amount of heat stored by the heat capacity of the material, $Q_{generated}$ is the amount of heat generated by the volume of material, $Q_{in}$ is the heat transferred into the material from its surroundings and $Q_{out}$ is the heat transferred to the surroundings; and ii) the cooling curves recorded by said first and second temperature sensors (10, 12);

the computer being set up to identify a time value $t_p$, corresponding to a local maximum of the heat generated in the centre of the sample as a fiction of time;

the computer being set up to calculate the maximum value of the first time derivative of the cooling curve recorded by the first temperature sensor (10) and to assign this value to the variable α and to assign the corresponding time to the variable $t_\alpha$;

the computer being set up to compare time values $t_p$ and $t_\alpha$, and if $t_{\alpha-tp}$ is less than a threshold value tv the computer being set up to identify a new first derivative value α, located at a time value $t_{\alpha 1}$, which is larger than $t_\alpha$, and which corresponds to a part of the cooling curve recorded by the first temperature sensor (10) where the second time derivative is approximately 0 and to assign this new first derivative value to the variable α;

the computer being set up to determine an amount value (Va) of a structure modifying agent to be added to the melt by using the first derivative value α and pre-recorded calibration data.

6. A computer program product for use in an apparatus for establishing, in real time, an amount of a structure-modifying agent to be added to a cast iron melt (20) during the process of producing a compacted graphite iron casting;

wherein the apparatus has a first temperature sensor (10) for recording a cooling curve in the centre of a sample vessel;

a second temperature sensor (12) for recording a cooling curve in the vicinity of the sample vessel wall;

a computer device (14) for determining an amount value (Va) of a structure modifying agent to be added to the melt;

a memory means (16) which is provided with pre-recorded calibration data;

the computer program product comprising:

a recording medium and a computer-readable code means for directing the computer device to determine the heat generated in the centre of the sample as a function of time (a heat generation curve) by applying i) the thermal balance formula:

$$Q_{stored} = Q_{generated} + Q_{in} - Q_{out}$$

where $Q_{stored}$ is the amount of heat stored by the heat capacity of material, $Q_{generated}$ is the amount of heat generated by the volume of material, $Q_{in}$ is the heat transferred into the material from its surroundings and $Q_{out}$ is the heat transferred to the surroundings; and the cooling curves recorded by said first and second temperature sensors (10, 12);

a recording medium and a computer-readable code means for directing the computer device to identify a time value $t_p$ corresponding to a local maximum of the heat generated in the centre of the sample as a function of time;

a recording medium and a computer-readable code means for directing the computer device to calculate the maximum value of the first time derivative of the cooling curve recorded by the first temperature sensor (10) and to assign this value to the variable a and to assign the corresponding time to the variable $t_\alpha$;

a recording medium and a computer-readable code means for directing the computer device to compare time values $t_p$ and $t_\alpha$, and if $t_\alpha - t_p$ is less than a threshold value tv to identify a new first derivative value α, located at a time value $t_{\alpha 1}$, which is larger than $t_\alpha$, and which corresponds to a part of the cooling curve recorded by the first temperature sensor (10) where the second time derivative is approximately 0 and to assign this new first derivative value to the variable α;

a recording medium and a computer-readable code means for directing the computer device to determine an amount value (Va) of a structure modifying agent to be added to the melt by using the first derivative value α and pre-recorded calibration data.

* * * * *